United States Patent

Fujii et al.

[11] Patent Number: 5,672,874
[45] Date of Patent: Sep. 30, 1997

[54] INFRARED OIL-CONCENTRATION METER

[75] Inventors: Hiroshi Fujii; Ryosuke Fukushima; Tatsuhide Tsutsui; Masahiko Ishida; Shuzi Takada, all of Kyoto, Japan

[73] Assignee: Horiba, Ltd., Kyoto, Japan

[21] Appl. No.: 413,633

[22] Filed: Mar. 30, 1995

[30] Foreign Application Priority Data

Mar. 30, 1994 [JP] Japan ............ 6-085459

[51] Int. Cl.⁶ ............ G01N 21/35; G01N 33/26
[52] U.S. Cl. ............ 250/343; 250/345; 250/339.12
[58] Field of Search ............ 250/343, 345, 250/349, 350, 339.12

[56] References Cited

U.S. PATENT DOCUMENTS

| | | | |
|---|---|---|---|
| 2,883,343 | 4/1959 | Favre et al. | 250/345 X |
| 4,101,221 | 7/1978 | Schunck et al. | 250/343 X |
| 4,204,424 | 5/1980 | Walker | 250/345 X |
| 4,567,366 | 1/1986 | Shinohara | 250/339.13 |
| 5,124,553 | 6/1992 | Hilliard et al. | 250/339.12 X |

FOREIGN PATENT DOCUMENTS

| | | | |
|---|---|---|---|
| 58-135940 | 8/1983 | Japan | 250/345 |
| 04478 | 10/1985 | WIPO . | |

OTHER PUBLICATIONS

Japanese Industrial Standard, Fuel Oil, JIS K 2205-1991.

*Primary Examiner*—Carolyn E. Fields
*Assistant Examiner*—Edward J. Glick
*Attorney, Agent, or Firm*—Price, Gess & Ubell

[57] ABSTRACT

An oil concentration meter includes a sample cell for receiving an oil sample that can be irradiated with infrared rays from a light source. A first interference filter having a design wavelength of 3.4 µm is positioned before a measuring detector, while a second interference filter transmitting a band range between 1 µm and 5 µm is positioned in front of a reference detector. A logarithm of the ratio of the reference detector output to the measuring detector output is used for determining the oil concentration in a sample.

12 Claims, 4 Drawing Sheets

INFRARED OIL-CONCENTRATION METER

BACKGROUND OF THE INVENTION

1. Field of the Invention

The present invention relates to an oil-concentration meter and more particularly to a simplified infrared oil-concentration meter assembly that can measure the concentration of oil in a sample, such as fuel oil.

2. Description of Related Art

An oil-concentration meter, as shown in FIG. 4, has been conventionally used as a device for measuring a concentration of fuel oils contained in, for example, a drainage system. Referring to FIG. 4, reference numeral 41 designates a cell bench provided with a sample cell 42 and a reference cell 43 arranged in parallel therewithin. The cell 41 and the cell 53 are sealed with a cell window 42a and a cell window 43a, respectively, made of highly infrared ray-transmissive materials, respectively, at both ends thereof and provided with a sample inlet 42b and a sample outlet 42c for supplying and discharging, respectively, a sample X obtained by extracting oils (HC components) with, for example, suitable extracting solvents. In addition, the reference cell 43 is filled with nitrogen gas 43b, which does not absorb any band of infrared rays as a reference sample.

Reference numeral 44 designates a light source portion provided on one side of the cell bench 41 and comprising two separate light sources 45 and 46 radiating infrared rays so as to correspond to the sample cell 42 and the reference cell 43, respectively. Thus, a so-called two-cell and two-light source-type structure is formed. An interference filter 47, 48 for a design wavelength of 3.4 μm, at which an absorption band for the oils exists, is provided in each optical path. In addition, reference numeral 49 designates an optical chopper for intermitting infrared rays from the respective light sources 45, 46, and reference numeral 50 designates a driving motor.

Reference numeral 51 designates a condenser microphone-type detector provided on the other side of the cell bench 41 and provided with two light-receiving chambers 51b, 51c partitioned with a partition wall 51a so as to correspond to the sample cell 42 and the reference cell 43, respectively. Reference numeral 52 designates an amplifier suitably amplifying an output from the condenser microphone-type detector 51. An output from the amplifier 52 is processed in a signal-operating portion (not shown).

Reference numeral 53, 54 designates a shielding plate provided between the light source portion 44 and the cell bench 41 and between the cell bench 41 and the condenser microphone-type detector 51, respectively, for providing a balance between two light sources in quantity of light. The shielding plates are provided to compensate for fluctuations in the respective light sources.

In an oil-concentration meter having the above described construction, upon supplying the sample cell 42 with a sample S under the condition that the light sources 45, 46 are switched on and the optical chopper 49 is being operated, infrared rays, which are transmitted through the reference cell 43, are incident upon the light-receiving chamber 51c of the condenser microphone-type detector 51 without being absorbed as a light having an intensity of $I_0$, while infrared rays, which are transmitted through the sample cell 42, are absorbed by the oils contained in the sample S to be incident upon the light-receiving chamber 51b as a light having an intensity of I. A partition wall 51a is formed as a diaphragm that can be relatively moved by a pressure difference between the respective light receiving chambers 51b and 51c, resulting from the transmission of the infrared rays into the respective chambers. Consequently, a difference $I_0-I$ is put out from the condenser microphone-type detector 51 and the concentration of the oils contained in the sample S can be obtained by a signal processing of this output.

However, in the above described conventional oil-concentration meter, the sample cell 42 and the reference cell 43 are arranged in parallel. A pair of light sources 45, 46 radiating these two cells 42, 43, respectively, and the condenser microphone-type detector 51 is used so that such a device is complicated and expensive.

The interference filter 47, provided in the optical path on the side of the sample cell 42 (optical path on the measuring side), and the interference filter 48, provided in the optical path on the side of the reference cell 43 (optical path on the standard side) are formed of filters having the same absorption wavelength band, so that, in the case where absorptions by components other than the oils occur, a disadvantage has occurred in that a standard light source in the strict sense of the word cannot be obtained and thus an error is apt to be produced due to changes, such as drifts of the light sources 45, 46 and contaminations of the cell windows and within the cells (hereinafter referred to as merely contamination of cells), over a lapse of time.

In addition, a disadvantage has occurred also in that the oil-concentration is obtained on the basis of the output $I_0-I$ from the condenser microphone-type detector 51 but an increased error can be produced in the vicinity of the span of the output $I_0-I$ in the case where the outputs from the light sources 45, 46 are fluctuated.

Furthermore, in the measurement, the handling has been considerably troublesome, for example, the quantities of light from the light sources 45, 46 must be precisely adjusted to be in balance. There is still a need in this field to have an accurate and relatively inexpensive oil meter arrangement.

OBJECTS AND SUMMARY OF THE INVENTION

The present invention has been achieved in view of the above described matters and it is an object of the present invention to provide an oil-concentration meter which is simple in construction and inexpensive and is not influenced by changes, such as deteriorations of light sources, during an operation time period. The instrument must further be capable of conducting a measurement with high accuracy, with a minimal adjusting operation and simple to use.

In order to achieve the above described object, an oil-concentration meter according to the present invention is characterized in that a light source applying infrared rays to a cell, where a sample containing oils in solvents is supplied, is arranged on one end side of the cell. A measuring detector and a reference detector receiving infrared rays, which have been transmitted through the cell, respectively, are provided on the other end side of the cell. A first interference filter transmitting merely absorption wavelengths of oils therethrough is provided in an optical path of the measuring detector, and a second interference filter providing a flat transmission characteristic over a wide band, including the band of absorption wavelengths of the oils is provided in an optical path of the reference detector.

In this case, provided that an output from the measuring detector is I and that from the reference detector is $I_0$, it is preferable that an oil-concentration is determined on the basis of $I_0/I$. It is preferable that one light source, one cell, one measuring detector, and one reference detector are used.

In addition, it is preferable that the first interference filter is formed of an optical filter having a central wavelength of 3.4 µm and a half-width of about 9% (about 0.3 µm), while the second interference filter is formed of an optical filter having a transmittance of 20% or less within a band of 1 µm to 5 µm.

Furthermore, it is preferable that, for example, a light-intermitting chopper is provided in the optical path from the light source to the detector to conduct a modulation.

In an oil-concentration meter having the above described construction, merely one light source is provided for one cell, so that any error of measurement resulting from a drift of the light source, a contamination of a cell and the like can be eliminated, and, the first interference filter transmitting merely the absorption wavelengths of the oils therethrough is provided in the optical path of the measuring detector while the second interference filter showing a flat transmission characteristic over a wide band including the absorption wavelengths of the oils is provided in the optical path of the reference detector, so that any influences by absorptive components other than the oils can be eliminated and thus a highly accurate measurement can be achieved even though they may exist in the instrument.

With the above described oil-concentration meter, a difference between an output on the standard side and that on the measuring side is not taken as in the conventional meter, but rather their ratio is taken, so that no error of measurement is produced, even though a quantity of light in the light source may fluctuate. In addition, the meter is simplified in construction and inexpensive while no adjusting operation is required for the light source and the operation of the instrument is made easy.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide an optical oil-concentration meter.

Figure 1:
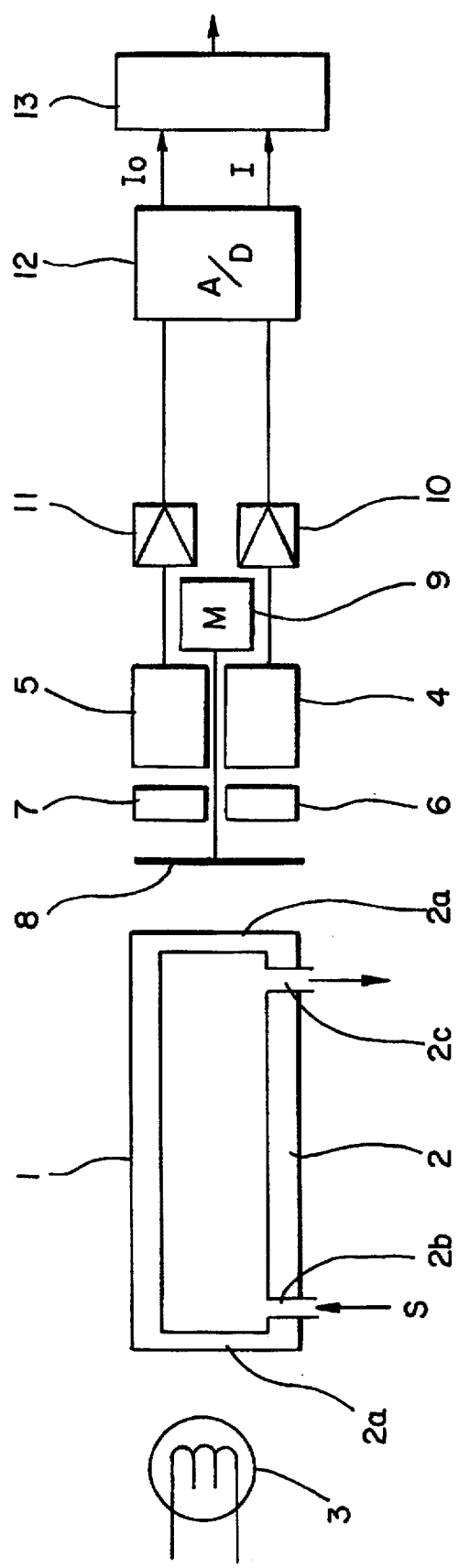
FIG. 1 is a block diagram roughly showing one example of an oil-concentration meter according to the present invention.

FIG. 1 is a drawing roughly showing one example of a construction of an oil-concentration meter according to the present invention. Referring to FIG. 1, reference numeral 1 designates a cell bench provided with one cell 2 therewithin. This cell 2 is made of highly corrosion-resistant materials, such as stainless steel, and sealed with a cell window 2a made of highly infrared ray-transmissive materials (for example, quartz) at both ends thereof and is additionally provided with a sample inlet 2b and a sample outlet 2c for supplying and discharging, respectively, a sample S obtained by extracting oils (HC components) with, for example, extracting solvents, such as Flone S-316.

Figure 2:
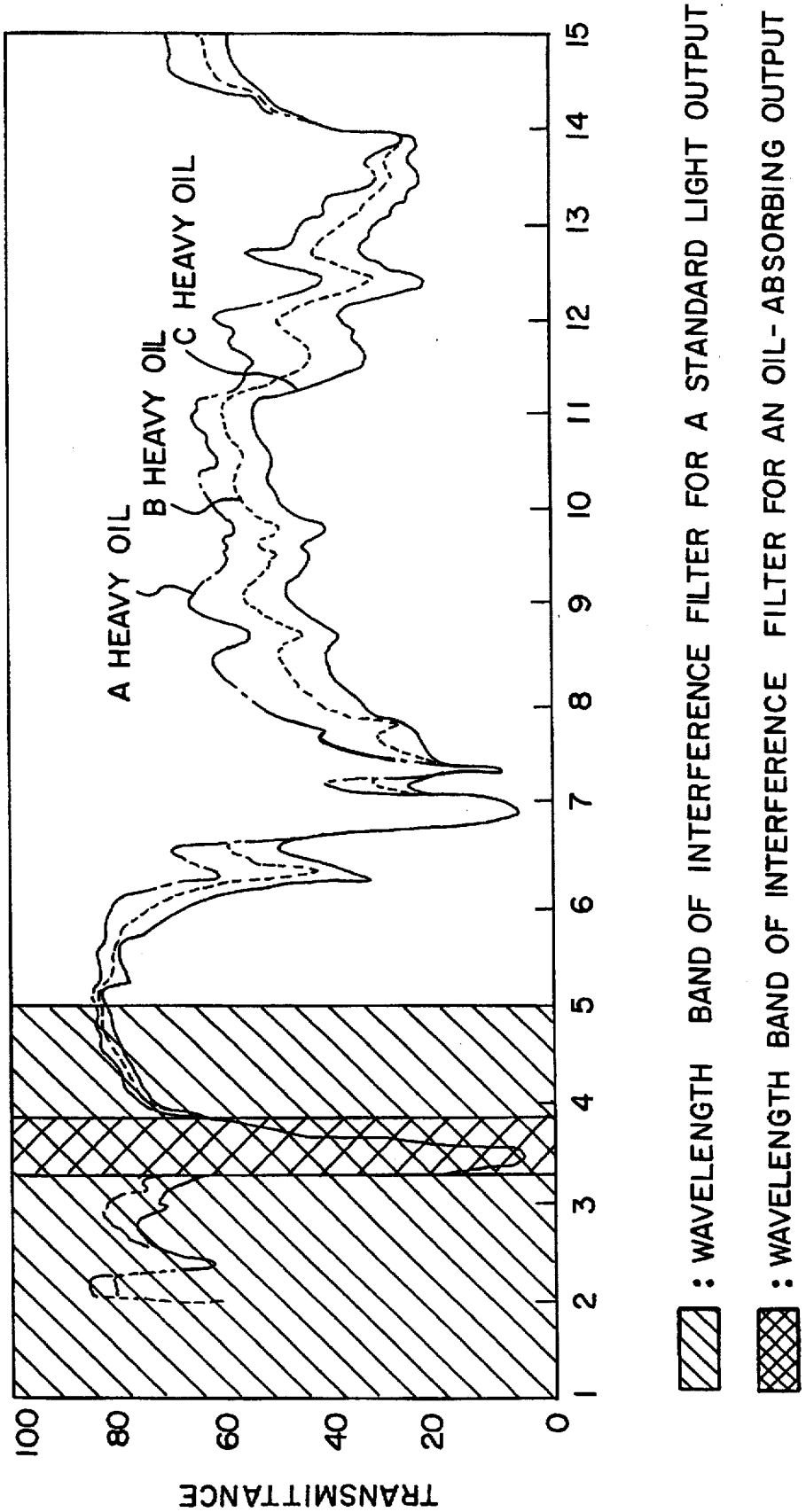
FIG. 2 is a drawing showing one example of an absorption spectrum obtained when a heavy oil-concentration was measured by the use of such an oil-concentration meter.
Figure 3:
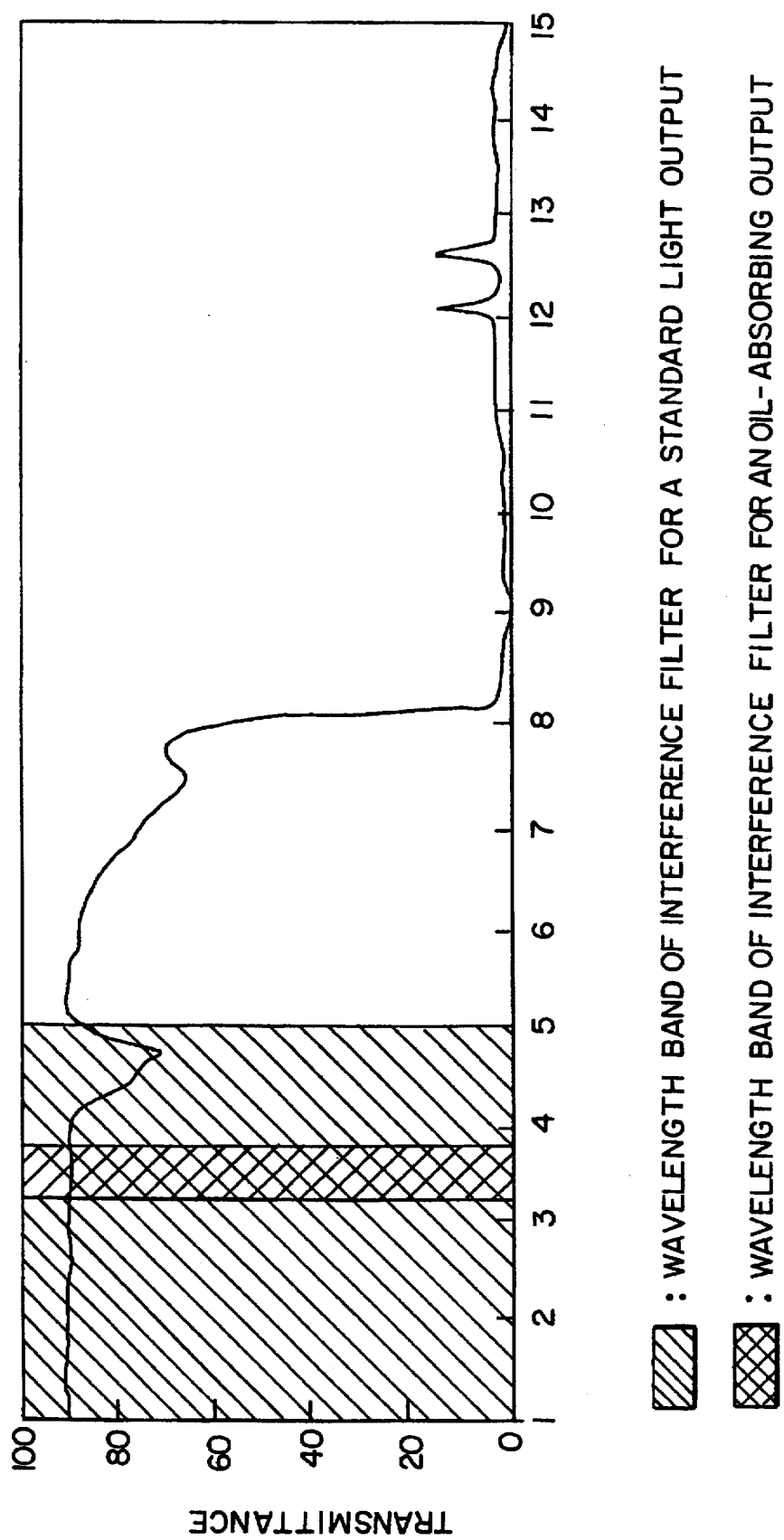
FIG. 3 is a drawing showing an absorption spectrum of Flone S-316 uses as an extracting solvent.

FIG. 3 discloses the absorption characteristics of Flone S-316. The sample S will be a mixture of Flone S-316 and a heavy fuel oil in order to obtain the absorption characteristics disclosed in FIG. 2. Flone S-316 has an absorption characteristic which is relatively flat within a band width of 5 µm or less, as shown in FIG. 3.

Reference numeral 3 designates a light source provided on one side of the cell bench 1 for applying infrared rays to the cell 2. Reference numerals 4, 5 designate a measuring detector and a reference detector provided in parallel on the other side of the cell bench 1. Both the measuring detector 4 and the reference detector 5 are formed of, for example, a pyroelectric infrared detector. A first interference filter 6 for a wavelength of 3.4 µm, at which a significant absorption band by the heavy oils exists, is provided on the light-receiving side of the measuring detector 4. In particular, this first interference filter 6 is an optical filter having a central wavelength of 3.4 µm and a half-width of about 9% (about 0.3 µm, which is about two times the conventional one).

In addition, a second interference filter 7 showing flat transmission characteristics over a wide band (for example 1 to 5 µm), including the absorption wavelength of 3.4 µm by the oils is provided on a light-receiving side of the reference detector 5. In particular, this second interference filter 7 is a wide band pass filter (an optical filter) having a transmittance of 20% or less within a band of 1 µm to 5 µm.

The reason why the second interference filter 7, formed of a wide band pass filter, is provided in the optical path of the reference detector 5 is that background noise resulting from a fluctuation of the light source 3 and the like can be reduced by utilizing lights within a wavelength band as wide as possible. In short, by using the wide band pass filter, an output from the reference detector 5 (an output of the standard light) is integrated within a transmission wavelength band to be proportional to the transmission wavelength band. In this case, also absorption wavelengths by the oils are transmitted but their output level is about ⅒ times the total. Consequently, also influences by some fluctuations within its wavelength band amount to ⅒ times ones for the total standard lights, even though they occur and thus they can be disregarded.

FIG. 2 shows the transmittance versus the wavelengths, µm, of various types of heavy oil, e.g., A, B, and C. Usually, heavy oils, such as fuel oils are classified by their kinematic viscosity. The characteristics and testing procedures for fuel oil are standardized according to Japanese Industrial Standards, such as JIS K 2205 (1991).

Reference numeral 8 designates an optical chopper provided between the cell bench 1 and the interference filter 6, 7. The optical chopper 8 is driven by means of a motor 9 to intermit infrared rays, which have passed through the cell 2, a appointed cycles.

Reference numerals 10, 11 designate a preamplifier suitable operating upon the output from the measuring detector 4 and the reference detector 5, respectively. Reference numeral 12 designates an amplifier for both amplifying and providing an A/D conversion of an output of the preamplifier 10, 11, respectively, and reference numeral 13 designates an operation portion comprising a microcomputer and the like. In the operating portion 13, log ($I_0/I$) is calculated from a signal of I on the side of the measuring detector 4 and a signal of $I_0$ on the side of the reference detector 5 and the oil-concentration can be obtained on the basis of the log ($I_0/I$).

In an oil-concentration meter having the above described construction, an oil-absorbing wavelength band output I by the fuel oils contained in the sample S is put out from the measuring detector 4. In addition, a standard light output $I_0$ proportional to the transmitted infrared rays integrated within the band of 1 to 5 µm is output from the reference detector 5. In this case, also the oil-absorbing wavelengths are transmitted to the standard light side but their output level amounts to about 1/10 times the total one, as shown in FIG. 2, so that it can be disregarded. And, in the operating portion 13, the oil-concentration contained in the sample S can be obtained by the calculating log ($I_0/I$, the calculation of absorptivity).

Heavy fuel oils are mixtures of various kinds of hydrocarbons, for example, A heavy oil, B heavy oil, and C heavy oil can show different spectra, as shown in FIG. 2, due to their differences in composition. In particular, when a wavelength band is 5 µm or more, the respective heavy oils can show marked differences in absorption of infrared rays, as shown in FIG. 2. Consequently, a wavelength band of 5 µm or more is cut by using the second interference filter 7 provided in the optical path of the reference detector 5. On the other hand, the respective heavy oils do not show increased changes in absorption at 3.4 µm. The second interference filter 7 shows a flat transmission characteristic in the wide wavelength band of 1 to 5 µm in FIG. 2, while the first interference filter 6 shows the transmission characteristics in the wavelength band of 3.4 to 4 µm. It can be understood from FIG. 2 that the second interference filter 7 has a bandwidth of 4 µm (5 µm–1 µm) and the first interference filter 6 has a bandwidth of about 0.4 µm (3.8 µm–3.4 µm) so that the ratio of the transmission of the second interference filter 7 to that of the first interference filter 6 is 10:1.

How, in the case where the heavy oils are not contained at all, infrared rays are not absorbed by the cell 2, so that the detecting energy in the detector 5 is "1" and that in the detector 4 is "1". On the other hand, in the case where the heavy oil (for example, A heavy oil) is contained in the sample S, the infrared rays, which have transmitted through the cell 2, are partially absorbed by the heavy oil and the remaining infrared rays are received by the detector 5 through the second interference filter 7, and output to the amplifier 11. Similarly, infrared rays are received by the detector 4 through the first interference filter 6 and output to the amplifier 10.

At this time, the quantity of infrared rays absorbed (the change in quantity of infrared rays) in the detector 5 is the same as that in the detector 4. Provided that this change in quantity of infrared rays is for example 0.5, the detecting energy of the detector 5 is 9.5 (=10–0.5), while the detecting energy of the detector 4 is 0.5 (=1–0.5).

In summary, in the case where the heavy oils are contained in the sample S, merely 0.5 of the detecting energy absorbed by the heavy oils within the cell 2 and the remaining infrared energies are detected by the detectors 5, 4.

Figure 4:
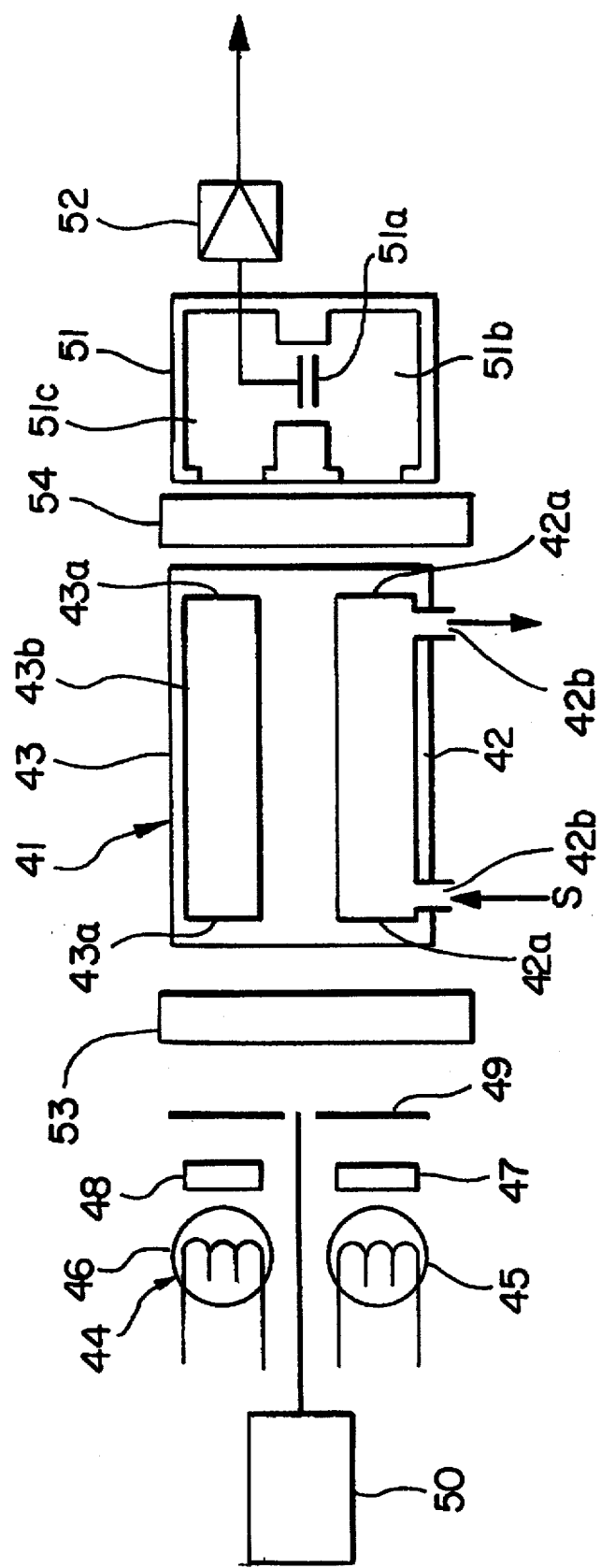
FIG. 4 is a block diagram roughly showing a conventional oil-concentration meter.

At this time, the output on the measuring side is changed from 1 to 0.5, while the output on the standard light side is changed from 10 to 9.5. The change in output amounts to 50% (=0.5÷1×10%) on the standard side, so that the output on the standard light side is influenced by merely 1/10 as compared with that on the measuring side. Consequently, even though infrared rays having the oil-absorbing wavelengths are transmitted onto the standard light side, their output level is about 1/10 of the total output level, so that they are almost negligible., A heavy oil, B heavy oil, and C heavy oil are almost the same in absorption characteristic within the wavelength band of 3.4 to 4 µm, so that not only the first interference filter 6 having this bandwidth is used but also the second interference filter 7, of which absorption characteristics of A heavy oil, B heavy oil, and C heavy oil have the bandwidth of 5 µm or less, including the wavelength band of 3.4 to 4 µm, is used. Conventionally, a filter having the absorption characteristics of 4 to 5 µm have been used as the interference filter 48 in FIG. 4, so that various kinds of problems have occurred.

In the above described oil-concentration meter, merely one light source 3 is provided for one cell 2, so that any error of measurement resulting from a drift of the light source 3, the contamination of cell 2 and the like can be eliminated. The first interference filter 6 transmitting merely the absorption wavelengths by the oils therethrough is provided in the optical path of the measuring detector 4 while the second interference filter 7 showing flat transmission characteristics over a wide band including the absorption wavelengths by the fuel oils is provided in the optical path of the reference detector 5, so that any influences by absorptive components other than the oils can be eliminated and thus a highly accurate measurement can be achieved, even though they may exist.

With the above described oil-concentration meter, a difference between the output $I_0$ on the standard side and that of I on the measuring side is not used as in the conventional meter, but rather log ($I_0/I$) is calculated in the operating portion 13, such as a microcomputer, so that the calculation of absorptivity can be conducted more accurately when compared with a conventional meter. In addition, a minimum error of measurement is produced, even though a quantity of light in the light source 3 may fluctuate. Furthermore, the meter is simplified in construction and inexpensive, while no additional adjusting operation is required for the light source and the handling is made easy.

FIG. 2 is a graph showing one example of an absorption spectrum obtained when heavy oil-concentrations were measured by the use of the above described oil-concentration meter, and FIG. 3 is a graph showing an absorption spectrum of Flone S-316 used as the extracting solvent. As can be seen, this solvent is relatively non-absorbent to the desired infrared rays of 3.4 µm.

Besides, although the oil-concentration is determined on the basis of the calculation of log ($I_0/I$) in the above described preferred embodiment, a calculation of merely the ratio of $I_0/I$ may be used to linearize expressions of the second degree or more. In this case, the processing burden on the microcomputer can be lightened.

The present invention is not limited by the above described preferred embodiment, but can be modified in different ways. For example, the detectors 4, 5 are not limited by a pyroelectric infrared detector, but may be formed of other solid-state detectors, such as a semiconductor detector, and a condenser microphone detector. In addition, although it is not shown, a plurality of measuring detectors 4 may be provided and those detectors 4 may be provided with a plurality of interference filters which do not transmit the absorption wavelengths of certain oils therethrough and also a plurality of interference filters which transmit merely the specified wavelengths of the absorption wavelengths of the oils therethrough so that concentrations of a plurality of different kinds of oil can be separately measured.

Furthermore, the optical chopper 8 may be provided between the cell 2 and the light source 3. And, the light source 3 may be intermitted at the appointed cycles in place of the use of the optical chopper 8 to conduct the modulation.

As described above, according to the present invention, merely one light source is provided for one cell, so that any error of measurement resulting from a drift of the light source, the contamination of the cell and the like can be eliminated. The first interference filter transmitting merely the absorption wavelengths by the oils therethrough is provided in the optical path of the measuring detector while the second interference filter showing the flat transmission characteristics over a wide band, including the absorption wavelengths by the oils, is provided in the optical path of the reference detector, so that any influences by absorptive components other than the oils can be eliminated and thus a highly accurate measurement can be achieved even though they may exist.

With the above described oil-concentration meter, the difference between the output on the standard side and that on the measuring side is not taken as in the conventional meter, but their ratio is taken, so that no error of measurement is provided, even though the quantity of light in the light source fluctuates. In addition, the construction of the meter is simplified and inexpensive, while no adjusting operation is required for the light source and the handling is made easy.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. An oil-concentration meter comprising:
   a sample cell for receiving an oil sample;
   a light source for applying infrared rays to the sample cell, where a sample containing oils in solvents is supplied, said light source being arranged on one end side of said cell;
   a measuring detector and a reference detector for receiving infrared rays, which have been transmitted through the sample cell, respectively, are provided on the other end side of the sample cell;
   a first interference filter having an optical filter with a design wavelength of 3.4 μm which transmits only absorption wavelengths characteristics of said oil sample is provided in an optical path of said measuring detector; and
   a second interference filter having flat transmission characteristics over a range of 1 μm to 5 μm, including said absorption wavelengths by the oil sample is provided in an optical path of said reference detector, whereby the outputs of the measuring detector and the reference detector are used to determine the oil concentrations in the sample.

2. An oil-concentration meter as set forth in claim 1, in which the output from the measuring detector is I and that from the reference detector is $I_0$, and further comprising a means for determining an oil-concentration on the basis of $I_0/I$.

3. An oil-concentration meter as set forth in claim 2, in which only one light source, one cell, one measuring detector and one reference detector are used.

4. An oil-concentration meter as set forth in claim 3, in which a light-intermitting chopper is provided in an optical path from the light source to the detectors.

5. An oil-concentration meter as set forth in claim 2, in which said first interference filter has a half-width of about 9% (about 0.3 μm) while said second interference filter is formed of an optical filter having a transmittance of 20% or less within a band of 1 μm to 5 μm.

6. An oil-concentration meter as set forth in claim 2, in which a light-intermitting chopper is provided in an optical path from the light source to the detectors.

7. An oil-concentration meter as set forth in claim 1, in which only one light source, one cell, one measuring detector and one reference detector are used.

8. An oil-concentration meter as set forth in claim 7, in which said first interference filter has a half-width of about 9% (about 0.3 μm) while said second interference filter is formed of an optical filter having a transmittance of 20% or less, within a band of 1 μm to 5 μm.

9. An oil-concentration meter as set forth in claim 7, in which a light-intermitting chopper is provided in an optical path from the light source to the detectors.

10. An oil-concentration meter as set forth in claim 1, in which said first interference filter has a half-width of about 9% (about 0.3 μm) while said second interference filter is formed of an optical filter having a transmittance of 20% or less within a band of 1 μm to 5 μm.

11. An oil-concentration meter as set forth in claim 1, in which a light-intermitting chopper is provided in an optical path from the light source to the detectors.

12. A fuel oil concentration meter comprising:
   a light source of infrared light;
   a sample cell transmissive of the infrared light from the light source located on one side of the sample cell, and adapted to receive an oil sample;
   a measuring detector;
   a reference detector located on the other side of the sample cell with the measuring detector, the reference detector and the measuring detector receiving light from the light source which has passed through the sample cell;
   a first interference filter having a design wavelength of approximately 3.4 μm positioned between the measuring detector and the source;
   a second interference filter having a band pass of approximately 1 μm to 5 μm positioned between the reference detector and the source;
   means for providing digital output signals representative of the measuring detector output signal I, and the reference detector output signal $I_0$; and
   means for calculating a log ($I_0/I$) to determine the oil concentration in the oil sample.

* * * * *